(12) United States Patent
Benson

(10) Patent No.: US 11,324,413 B1
(45) Date of Patent: May 10, 2022

(54) TRAUMATIC BRAIN INJURY DIFFUSION TENSOR AND SUSCEPTIBILITY WEIGHTED IMAGING

(71) Applicant: CENTER FOR NEUROLOGICAL STUDIES, Novi, MI (US)

(72) Inventor: Randall R. Benson, Waterford, MI (US)

(73) Assignee: CENTER FOR NEUROLOGICAL STUDIES, Novi, MI (US)

( * ) Notice: Subject to any disclaimer, the term of this patent is extended or adjusted under 35 U.S.C. 154(b) by 221 days.

(21) Appl. No.: 16/523,189

(22) Filed: Jul. 26, 2019

Related U.S. Application Data

(63) Continuation of application No. 16/150,650, filed on Oct. 3, 2018, now abandoned, which is a continuation
(Continued)

(51) Int. Cl.
*A61B 5/026* (2006.01)
*A61B 5/00* (2006.01)
(Continued)

(52) U.S. Cl.
CPC .......... *A61B 5/0263* (2013.01); *A61B 5/0042* (2013.01); *A61B 5/4064* (2013.01); *A61B 5/725* (2013.01); *A61B 5/7246* (2013.01); *A61B 5/7282* (2013.01); *G01R 33/5602* (2013.01); *G01R 33/5608* (2013.01);
(Continued)

(58) Field of Classification Search
CPC ................ A61B 5/0263; A61B 5/7246; A61B 5/7282; A61B 5/725; A61B 5/4064; A61B 5/0042; A61B 2576/026; G01R 33/56341; G01R 33/5608; G01R 33/5602; G06T 7/0016; G06T 2207/30016; G06T 2207/10092
See application file for complete search history.

(56) References Cited

U.S. PATENT DOCUMENTS

2012/0141003 A1    6/2012  Wang

OTHER PUBLICATIONS

Field, Aaron; Filippi, Christopher; Kalnin, Andrew; Lipton, Michael; Mukherjee, Pratik and Welker, Kirk; ASFNR Guidelines for Clinical Application of Diffusion Tensor Imaging, Mar. 8, 2012.
(Continued)

*Primary Examiner* — Bo Joseph Peng
(74) *Attorney, Agent, or Firm* — Brooks Kushman PC

(57) ABSTRACT

A method to increase the reliability and clinical utility of diffusion tensor imaging (DTI) of traumatic brain injury (TBI) in single subjects and a semi-automated method of identifying and quantifying small hemorrhages using susceptibility-weighted images (SWI) of single subjects include storing an image template formed from control subjects, storing a brain image of the single subject, correcting for image acquisition differences of the control subjects and single subject, and performing regional analysis of the brain image of the single subject. The method may include analysis of fractional anisotropy values that are age-corrected between the control subjects and the single subject before performing voxel-based analysis (VBA), and a hybrid VBA and tract-based spatial statistical (TBSS) analysis with the VBA and TBSS results combined using a statistical calculation. The resulting combined DTI image may be further combined with an SWI image, FLAIR image, and/or T1 image of the single subject.

18 Claims, 15 Drawing Sheets

Related U.S. Application Data of application No. 15/233,545, filed on Aug. 10, 2016, now abandoned, which is a continuation of application No. 14/090,125, filed on Nov. 26, 2013, now abandoned.

(60) Provisional application No. 61/779,193, filed on Mar. 13, 2013.

(51) Int. Cl.
  *G01R 33/56* (2006.01)
  *G06T 7/00* (2017.01)
  *G01R 33/563* (2006.01)

(52) U.S. Cl.
  CPC ...... *G01R 33/56341* (2013.01); *G06T 7/0016* (2013.01); *A61B 2576/026* (2013.01); *G06T 2207/10092* (2013.01); *G06T 2207/30016* (2013.01)

(56) References Cited

OTHER PUBLICATIONS

Mahvash, M.; Konig, R.; Urbach, H.; Von Ortzen, J.; Meyer, B.; Schramm, J; and Schaller, C., Flair-/T 1-/T2-Co-Registration for Image-Guided Diagnostic and Resective Epilepsy Surgery, Neurosurgery, Feb. 2008, 62 Suppl 2; 482-8.

Stewart, Brent K., Introduction to MR Image Contrast, Retrieved from www.rad.washington.edu/academics.

Hesselink, John R., Basic Principles of MR Imaging, Retrieved Nov. 3, 2013, from spinwarp.ucsd.edu/neuroweb/Text/br-100.htm.

Ashburner, John et al., SPM8 Manual, The FIL Method Group, Functional Imaging Laboratory, Feb. 4, 2013.

Mori et al., Stereotaxic White Matter Atlas Based on Diffusion Tensor Imaging in an ICBM Template, NeuroImage, Apr. 1, 2008; 40(2): 570-582.

Oishi et al., Atlas-based whole brain white matter analysis using large deformation diffeomorphic metric mapping: Application to normal elderly and Alzheimer's disease participants, NeuroImage, Jun. 2009; 46(2): 486-499.

Prastawa et al., http://www.na-mic.org/Wiki/images/b/b3/NAMIC-ABC-UCLA-08Nov2010.ppt, Nov. 2010.

Jones et al., The effect of filter size on VBM analyses of DT-MRI data, NeuroImage 26 (2005) 546-554.

Chen et al.; Progression of White Matter Lesions and Hemorrhages in Cerebral Amyloid Angiopathy, Neurology, Jul. 11, 2006; 67(1):83-87.

Kou et al.; Susceptibility Weighted Imaging Complements Diffusion Tensor Imaging in Traumatic Brain Injury, Proc. Intl. Soc. Mag. Reson. Med. 17, 2009.

Somasundaram et al.; Fully Automatic Brain Extraction Algorithm for Axial T2-Weighted Magnetic Resonance Images, Computers in Biology and Medicine 40 (2010) 811-822.

Cohen et al.; Proton MR Spectroscopy and MRI-Volumetry in Mild Traumatic Brain Injury, AJNR AM J Neuroradiol 28: 907-13, May 2007.

Benson et al.; Detection of Hemorrhagic and Axonal Pathology in Mild Traumatic Brain Injury Using Advanced MRI: Implications for Neurorehabilitation, Sep. 2012, Neurorehabilitation, vol. 31, No. 3, pp. 261-279, 2012.

TRAUMATIC BRAIN INJURY DIFFUSION TENSOR AND SUSCEPTIBILITY WEIGHTED IMAGING

CROSS-REFERENCE TO RELATED APPLICATION

This application is a continuation of U.S. Ser. No. 16/150,650 filed Oct. 3, 2018, which is a continuation of U.S. Ser. No. 15/233,545 filed Aug. 10, 2016, which is a continuation of U.S. application Ser. No. 14/090,125 filed Nov. 26, 2013, which claims the benefit of U.S. provisional application Ser. No. 61/779,193 filed Mar. 13, 2013, the disclosures of which are hereby incorporated by reference in their entirety.

BACKGROUND

Technical Field

The present disclosure relates to the computer-implemented quantitative analysis of brain images generated using various imaging techniques including diffusion tensor imaging (DTI), fluid attenuated inversion recovery (FLAIR) imaging, and susceptibility-weighted imaging (SWI) to identify and diagnose traumatic brain injury.

Description of the Related Art

Conventional magnetic resonance imaging (MRI) is generally not sensitive enough to detect mild traumatic brain injury (mTBI), such as concussion. Unlike standard clinical MRI techniques, diffusion tensor imaging has demonstrated the ability to detect axonal injury in TBI patients. DTI data cannot be reliably interpreted simply by visual inspection due to lesions being small, signal changes being small, and variability in anatomy. As such, there is currently no uniform way to process DTI data. The mean fractional anisotropy (FA) for the total volume of white matter for a given patient has been shown to correlate with TBI severity, but does not reliably distinguish the mildest brain injuries from healthy, non-injured volunteers. In practice, there are several sources of false negative and/or false positive errors that render diagnosis of TBI in a single subject based on MRI techniques very difficult. These may include under sampling the variance of the control or reference group, poor registration between images of the controls and images of the patient, variation due to age effects between the controls and the patent, inability of various analysis techniques to isolate white matter from other tissue, and noise associated with various sources.

Similarly, in SWI, hemorrhages can be small venous hemorrhages and thus difficult to distinguish from veins. These, among other limitations, make these methods less useful clinically.

One limitation of DTI statistical analysis of scalar DTI images (i.e., Eigenvalue images, Fractional Anisotropy (FA) images or values, Apparent Diffusion Coefficient (ADC) images) has been the inability to compare a patient or a group of patients acquired using one scanner/protocol with another group of patients or controls acquired on a different scanner or which used a different protocol. Since the scanner/protocol can affect these DTI derived scalars, i.e., increasing or decreasing the values, a correction must be employed to eliminate these confounding or potentially artifactual results.

SUMMARY

One aspect of the present disclosure includes a method to increase the reliability and clinical utility of diffusion tensor imaging (DTI) of traumatic brain injury (TBI) in single subjects.

In various embodiments, a computer-implemented method of processing brain images for diagnosis of traumatic brain injury of a single subject in a clinical setting includes storing an image template formed from spatial normalization of a plurality of source brain images of a plurality of control subjects captured using two or more image acquisition devices including a first image acquisition device, storing a brain diffusion tensor (DT) image of the single subject acquired using the first image acquisition device, correcting for image acquisition differences among the two or more image acquisition devices using ratio normalization by calculating a ratio of a statistical parameter of images captured using the first image acquisition device to the statistical parameter of images captured using another of the two or more image acquisition devices, and performing regional analysis of the brain image of the single subject by generating a single subject statistical map based on differences between the brain image of the single subject relative to a statistical combination of the plurality of source brain images normalized using the image template. The method may include storing at least one additional brain image of the single subject acquired using at least one of susceptibility weighted imaging (SWI) and fluid attenuated inversion recovery (FLAIR) imaging, and combining the at least one additional brain image with the DT image of the single subject.

Some embodiments also include performing regional analysis by processing the brain image of the single subject to generate a single subject global white matter fractional anisotropy (FA) image, processing the plurality of source brain images to generate a control global white matter FA image, generating a tract-based spatial statistics (TBSS) map based on the single subject global white matter FA image relative to the control FA image, generating a voxel-based statistical map based on the single subject global white matter FA image relative to the control FA image, and generating a combined statistical map based on the TBSS map and the voxel-based map.

To adjust or correct for variations among MR scanners or other image acquisition devices and protocols, an image template may be calculated from a plurality of source images acquired using different image acquisition devices or protocols. Various embodiments may include performing nonlinear spatial normalization of each of a plurality of source brain images relative to a first standard template, calculating a statistical mean image of the plurality of normalized brain images associated with each image acquisition device, normalizing each of the plurality of source brain images to the statistical mean of a corresponding image acquisition device to generate an image acquisition device normalized mean image for each image acquisition device, and calculating the image template based on a statistical mean of all the image acquisition device normalized mean images.

Another aspect of the present disclosure includes a semi-automated method of identifying and quantifying small hemorrhages in susceptibility-weighted images (SWI) of single subjects.

In various embodiments, a computer-implemented method for processing brain images for diagnosis of traumatic brain injury of a single subject in a clinical setting includes storing an image template formed from combining a plurality of spatially normalized source brain images of a plurality of control subjects, storing a brain image of the single subject, and normalizing the brain image of the single subject using the image template formed from the plurality of control subjects. The method may also include calculating a statistical parameter, such as a standard score or z-score, that compares the brain image of the single subject to the image template for each voxel in each image to generate a statistical map of the single subject, applying at least one mask to the statistical map of the single subject to remove non-white matter and generate a white matter statistical map of the single subject, and calculating a volume of hemorrhagic lesions based on a number of voxels in the white matter statistical map where the statistical parameter exceeds a corresponding threshold.

In one embodiment, magnetic resonance imaging sequences are used to acquire T1, T2, SWI, and FLAIR images of a plurality of control subjects. The T2 images are normalized to a standard library template and combined to generate a transformation matrix applied to the SWI images to generate an SWI template. The single subject SWI image is normalized using the SWI template. The T1 and FLAIR images are used to generate white matter and cerebrospinal fluid (CSF) masks, respectively, that are applied to a statistical z-map of the single subject normalized SWI image to substantially remove all non-white matter prior to calculating the volume of hemorrhagic lesions.

DETAILED DESCRIPTION

Figure 1:
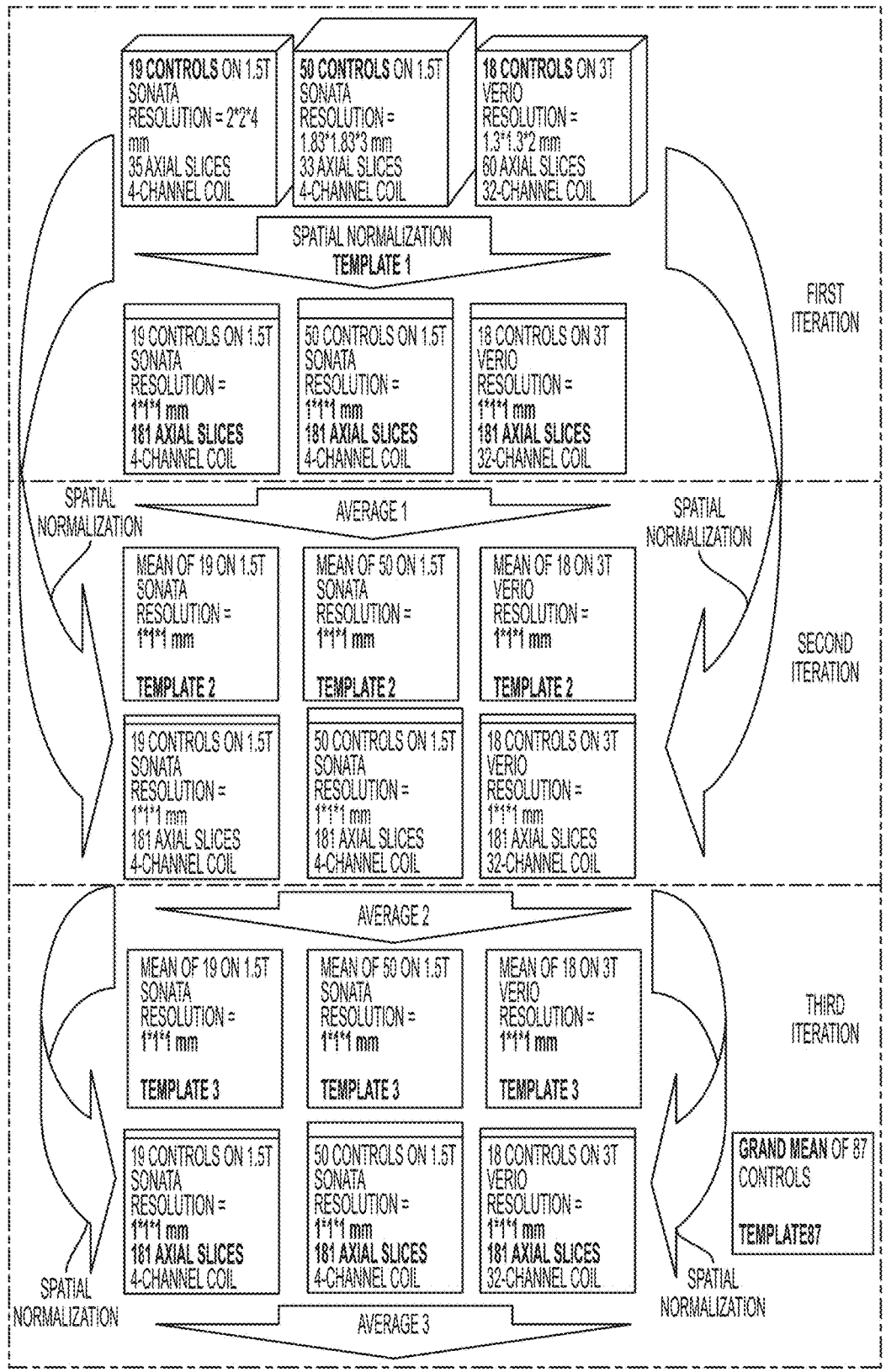
FIG. 1 illustrates a representative embodiment of an iterative process for creating a template generated using images from control subjects acquired using different image acquisition devices and/or protocols.

As required, detailed embodiments are disclosed herein; however, it is to be understood that the disclosed embodiments are merely exemplary of the claimed subject matter, which may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the claimed subject matter. As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations A first aspect of the disclosure is illustrated schematically in FIGS. 1-6. It relates to a method of quantitative diffusion tensor image analysis in single subjects with traumatic brain injury. The main steps are as follows, and need not be practiced in the sequence described, nor with the exact number of steps or sample sizes described.

1. Template Formation

To combine images across multiple subjects it is necessary to bring the images into a standard space. This step, known as spatial normalization (see FIG. 1) is critical for maximizing the accuracy of voxel-wise between-subject statistical comparisons.

Spatial normalization preferably is achieved with computer programs (e.g., SPM, FSL) which use a statistical cost-function to warp one image (the source image) into a standard or template image of the same type as the source image. The optimal template is an averaged image of several spatially normalized source images. This ensures that the template will have the spatial properties of the group from which it is derived, while minimizing the effects of subject-specific properties. This also ensures that the template will be robust or reliable for typical source images.

Oftentimes, templates of a particular type of scan are freely available through the internet but are only optimal for source images similar to those from which the template was constructed. In some cases it is necessary to compare groups of subjects acquired using different scanners or protocols. To maximize the spatial fit between the groups after normalization it may be preferable to iteratively normalize the images (see FIG. 1).

In one approach, the first iteration normalizes each subject to an external, freely available template (=Template 1). If we assume there are three groups of subjects—but not necessarily three—with (for example) 19, 50 and 18 subjects, respectively, then three group means can be created after the first iteration. The second iteration re-normalizes the native source images to the respective group mean (=Template 2). This creates a second set of normalized images from which three new group means can be created (Templates 3). The third iteration re-normalizes the native source images to Template 3, creating 87 normalized DTI images which are averaged together to form Template87. Using the original, native images in the second iteration minimizes interpolation error occurring with re-slicing images.

It will be appreciated that the number of controls, resolutions, slices, channel coils, and iterations are examples only; however, in general, a greater number of images is preferable assuming good quality images and transformations.

2. Correction for Scanner and Scanning Differences Between Groups or Subjects

One limitation of DTI statistical analysis of scalar DTI images (i.e., Eigenvalue images, Fractional Anisotropy (FA) images or values, Apparent Diffusion Coefficient (ADC) images) has been the inability to compare a patient or a group of patients acquired using one scanner/protocol with another group of patients or controls acquired on a different scanner or which used a different protocol. Since the scanner/protocol can affect these DTI derived scalars, i.e., increasing or decreasing the values, a correction must be employed to eliminate these confounding or potentially artifactual results.

Figure 2:
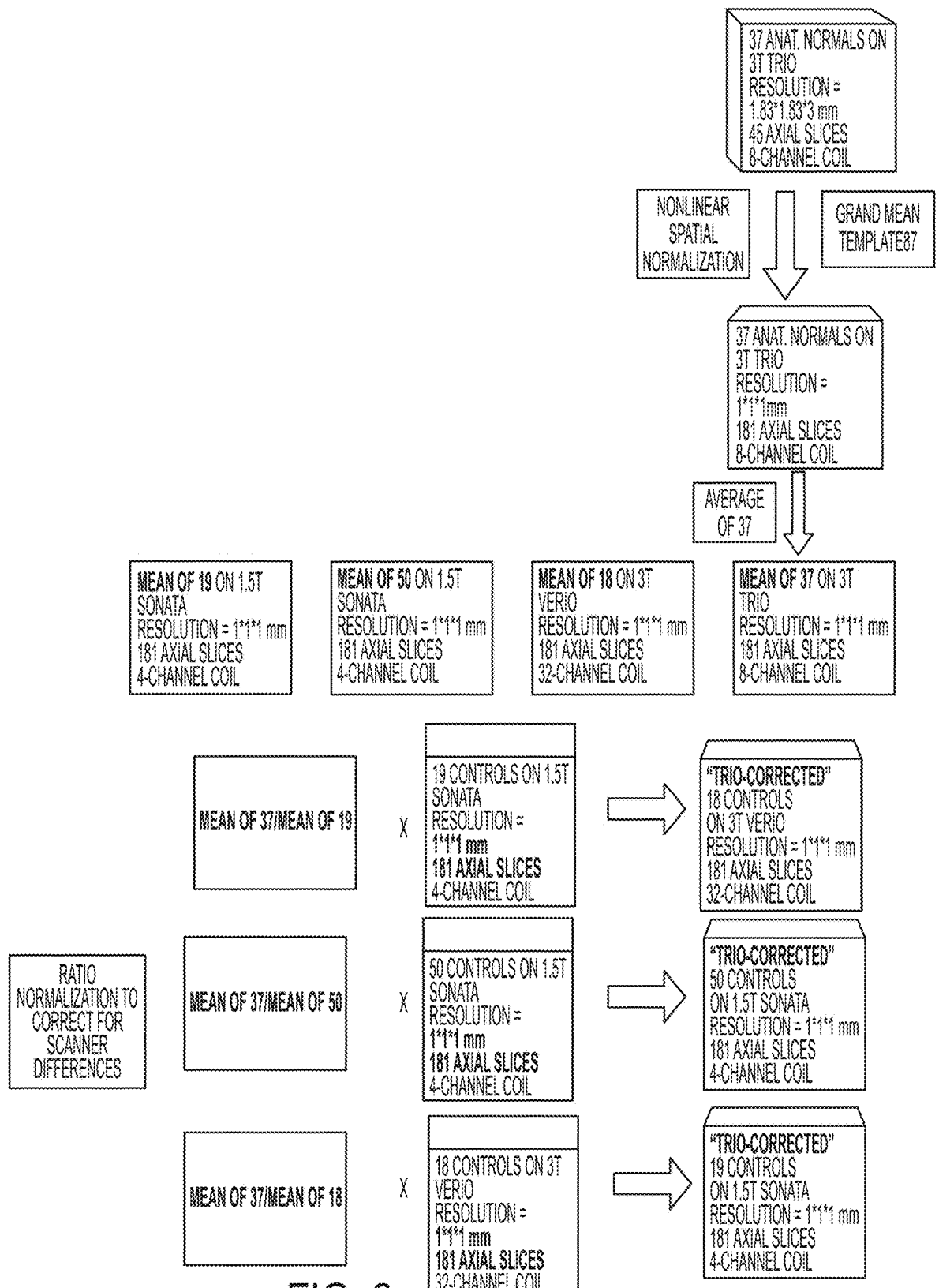
FIG. 2 illustrates correction for scanner and other scan-related differences using a template, such as the template created using the process of FIG. 1, in preparation for subsequent analysis according to embodiments of the disclosure.
Figure 3:
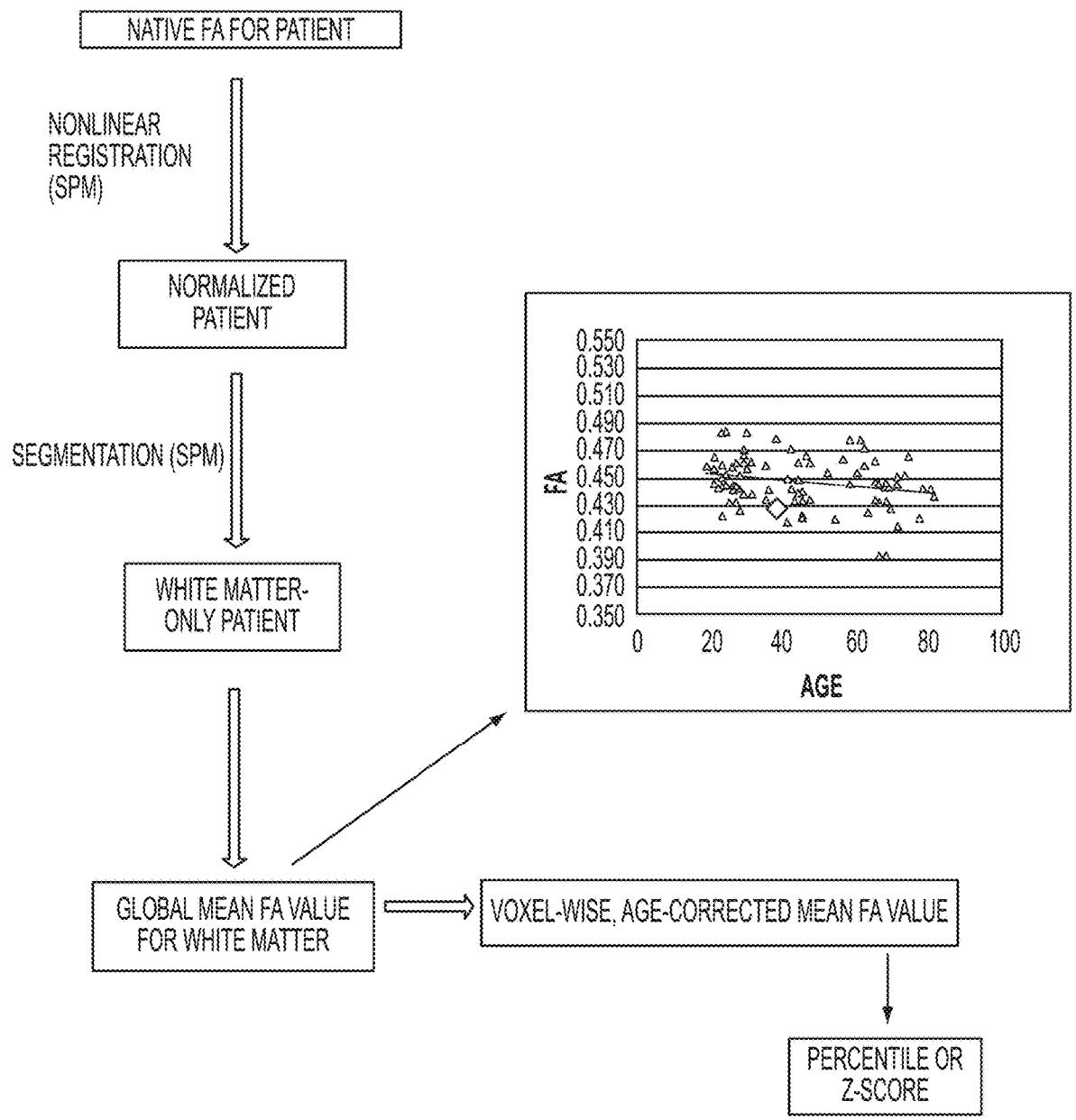
FIG. 3 illustrates correction for age differences between the source images for a control image and a single subject image according to embodiments of the disclosure.
Figure 4:
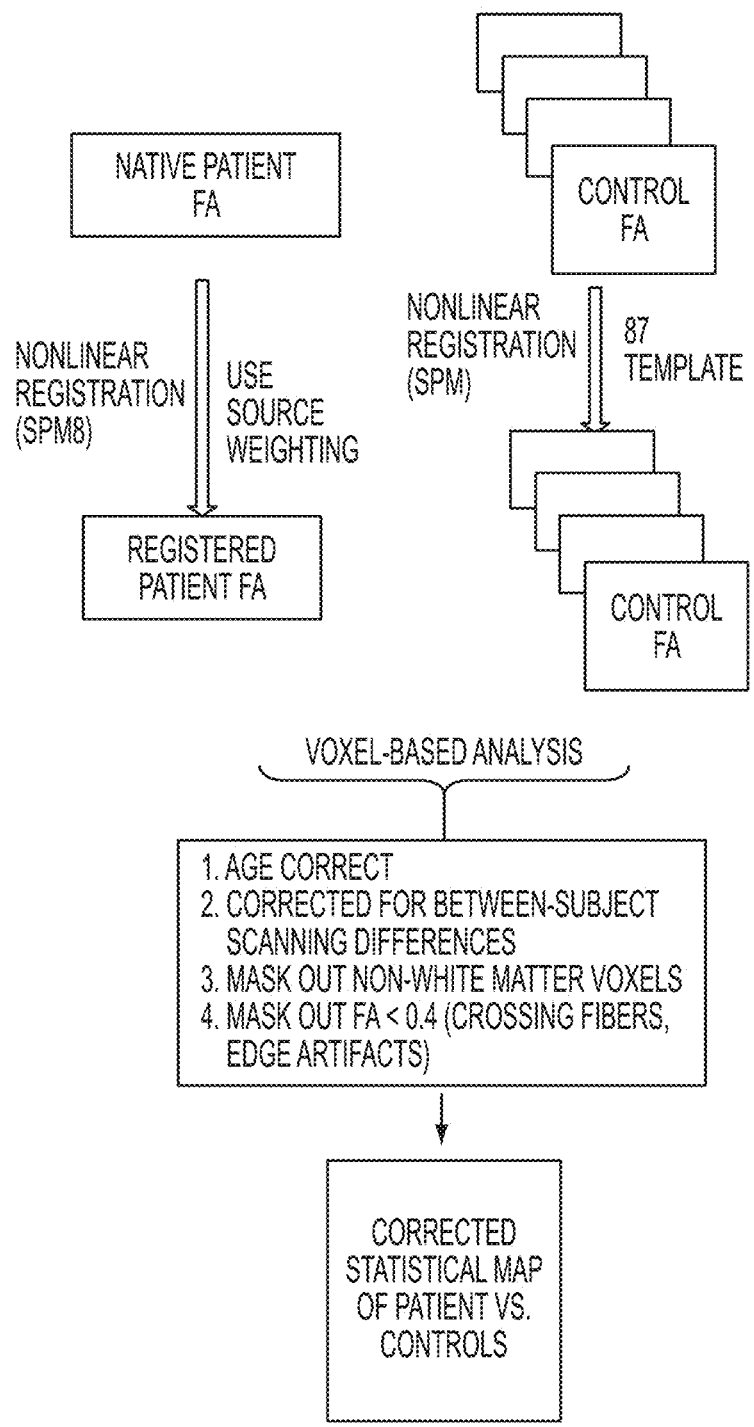
FIG. 4 illustrates a representative embodiment of voxel-based analysis of a single subject relative to a control image.
Figure 5:
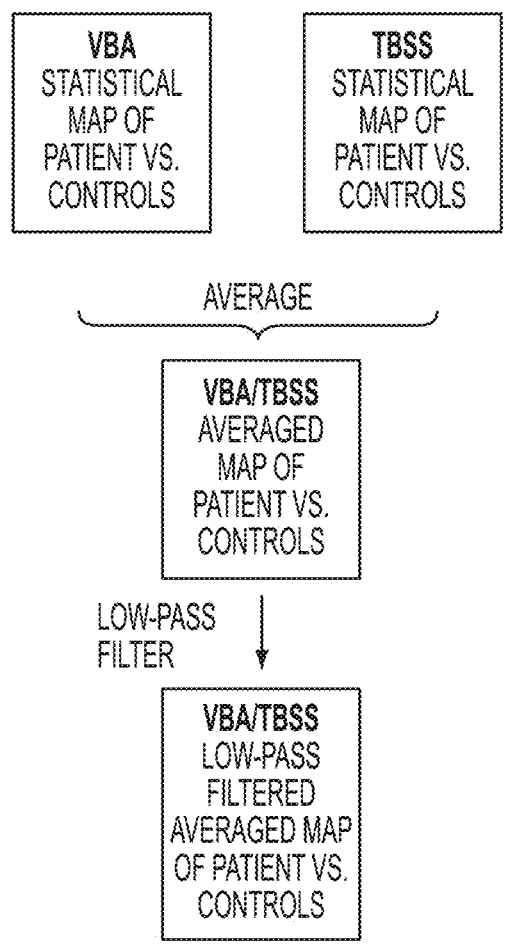
FIG. 5 illustrates a hybrid of voxel-based analysis and tract-based analysis of a single subject relative to a control image according to embodiments of the disclosure.
Figure 6:
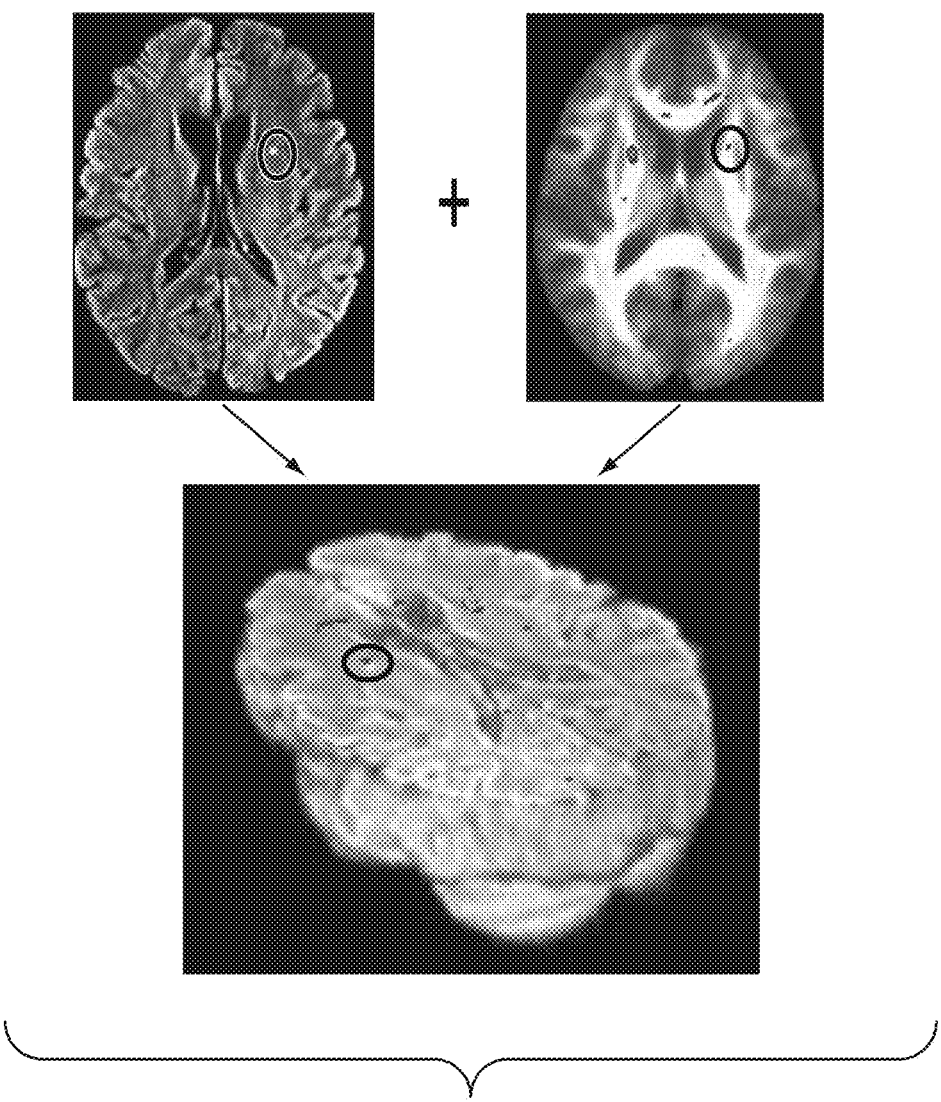
FIG. 6 illustrates co-registration and fusion of DTI and FLAIR images according to a representative embodiment of the disclosure.
Figure 7:
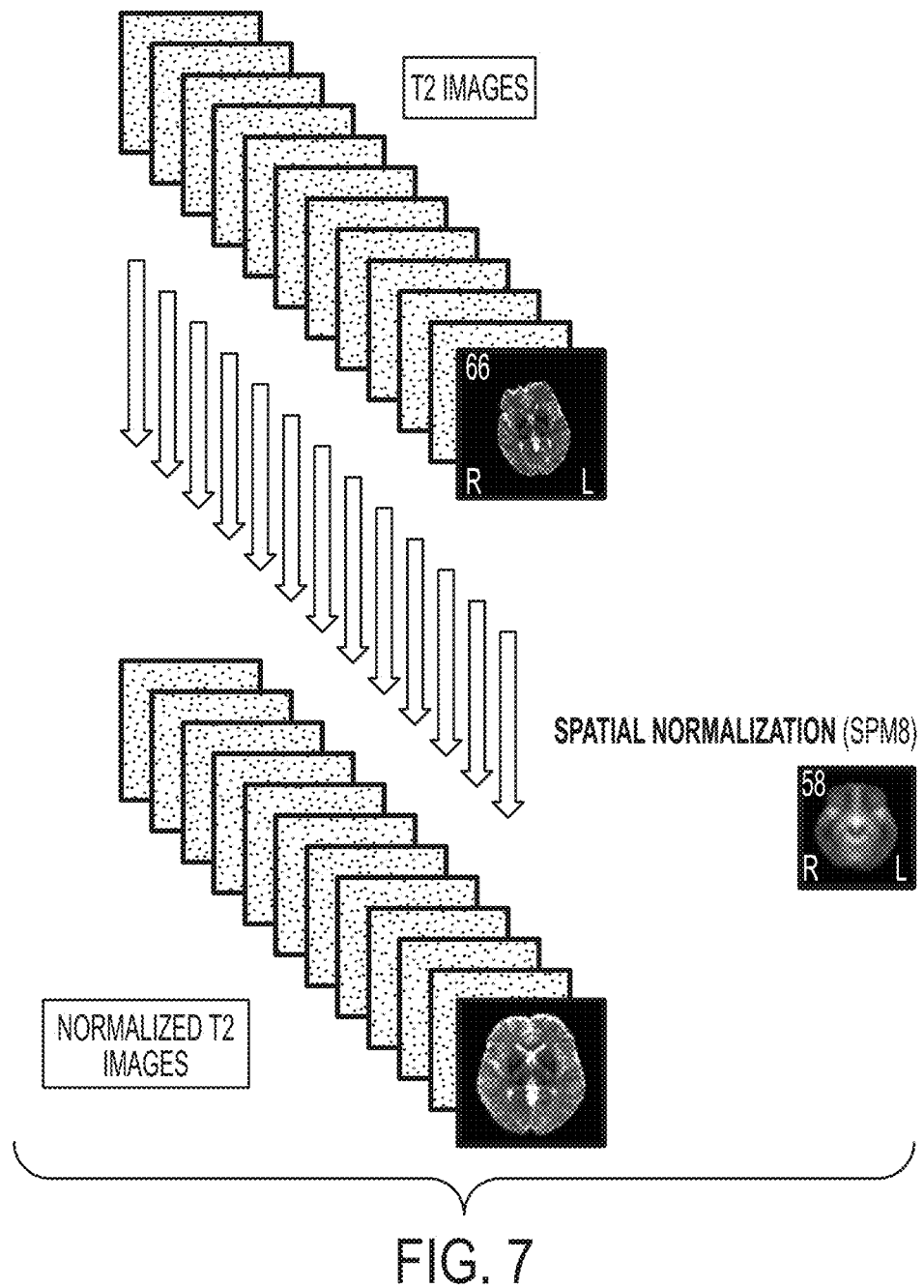
FIG. 7 illustrates spatial normalization of T2 images to a standard T2 template to generate a transformation matrix according to embodiments of the disclosure.

Provided there is an adequate number of subjects (preferably at least 10 per group), each subject's normalized DTI (i.e., fractional anisotropy or FA) image is multiplied by the ratio of the mean of desired scanner/protocol images to the mean of the subject's group (see FIG. 2). A sufficient number of samples from each protocol is necessary to adequately estimate the image properties of a respective scanner/protocol in order to correct for it.

While healthy controls are best for such a correction between platforms, a group of mild TBI brains without observable anatomical lesions may be used in this manner since the subtle, patchy and spatially non-uniform FA changes will average out and pale in comparison to significant scanner or protocol-related signal changes. This procedure allows for a more powerful analysis of cross-site data since control subject images can be combined to create much larger reference databases for comparison against individual patients or groups of patients.

3. Global White Matter FA Analysis

The majority of closed head injury results in traumatic axonal injury (synonymous with diffuse axonal injury or DAI). This pathology is multifocal or diffuse throughout the white matter of the brain and is a consequence of stretching, shear and compaction of the axons of the brain which comprise the white matter. Clinically, functional outcome is dictated by the severity or extent of axonal injury rather than focal injury, so that quantifying the extent or severity of white matter injury has important clinical utility for prognosis and potentially for driving treatment.

A. Correction For Age. To maximize the sensitivity of the global analysis, it is necessary to correct FA images for age (see FIG. 3). This is necessary since aging has been shown to cause a predictable linear decline in FA throughout the lifespan. One embodiment of the present disclosure uses voxel-wise correction for age effects. This embodiment uses the slope of the regression of FA from, for example, 87 healthy control subjects between 19 and 81 years of age. A mathematical correction of the global FA mean for a single subject or patient to the mean age of the control group ensures that age does not spuriously increase or decrease the global FA value.

B. Express Global FA Mean As Percentile Or Z-score Relative To 87 Controls—It is desirable to express a particular patient's global FA quantitatively, e.g., as a percentile or a z-score. As mentioned earlier, it is necessary or desirable to account for the age effect on global FA before calculating percentile or z-score. This embodiment of the present disclosure calculates the slope of the linear decrease in global FA for age and normalizes to the mean age prior to percentile and z-score calculation.

4. Regional Analysis

Due to insensitivity of the global method to mild TBI (mTBI), it is often necessary or desirable to use a higher resolution approach. Conceptually this is a consequence of sparser axonal pathology in mTBI compared with more severe TBI. A more useful approach is to divide the brain white matter into smaller units. Various embodiments according to the present disclosure incorporate two approaches, including: A) Voxel-based Analysis (VBA); and B) A hybrid of VBA and a tract based analysis, such as Tract-Based Spatial Statistics (TBSS) (See FIGS. 4-5).

A. Voxel-based Analysis (VBA). This mode of analysis assumes excellent spatial registration between a patient's FA image relative to the FA image of the controls. This then allows for valid statistical comparison (e.g., z-map) between voxels of the patient and voxels of the controls.

In practice, there are several sources of false negative and/or false positive errors. These include: 1) under sampling the variance of the control or reference group; 2) poor registration between patient and controls; 3) age effects: 4) ensure white matter only; and a 5) noise mask.

Disclosed herein are five optional steps which improve voxel-based analysis over extant methods (see FIG. 4):

1. Use a new template of (for example) 87 controls (T87). The spatial normalization function is preferably but not necessarily executed using SPM8. The T87 template creation is described above and a standard deviation map was also created from the same 87 control subjects 2. Use native FA image as "source weighting" for non-linear registration. This optimization step maximizes the match between patient and template white matter anatomy. FA is highest in white matter because of anisotropic diffusion in coherent bundles of axons so that empirically using the FA image itself to weight the normalization algorithm provides a better final match for white matter.

3. Voxel-wise age correction, Similar to the age correction of the global analysis above (3A), it is desirable or necessary to correct FA images for age. It has been shown that there is regional variation for the age effect on FA. Therefore, another variation of the present disclosure is a voxel-wise correction for the age effect. This embodiment uses the calculated slopes of the regression lines for each white matter voxel's FA from 87 healthy control subjects between 19 and 81 years of age. The slope then allows for mathematic correction of each voxel's FA value to the mean age of the control group, ensuring that age does not spuriously increase or decrease a voxel FA value.

4. Ensure white matter only. This step excludes voxels from either patient or the mean image of the 87 control images (T87) after each image is segmented into gray matter, white matter and cerebrospinal fluid using SPM8's segmentation tool. White matter probability maps for both images are thresholded at for instance P>0.55 to create binary masks of white matter and multiplied by the z-map to exclude any non-white matter voxels from the final z-map.

5. "Noise" mask. In order to reduce false positive error (artifactually reduced FA), which can occur as a result of reduced patient image quality, low native image resolution, edge artifacts and intravoxel fiber heterogeneity, a lower threshold of for example FA=0.4 is applied to a patient's FA map before statistical map generation.

B. Hybrid of voxel and tract based analytic approaches. As schematically portrayed in FIG. 5, these two analytic methods complement each other.

Tract-based spatial statistics (TBSS) spatially co-register between subjects using a search algorithm which identifies and then aligns common white matter tracts between subjects. Statistical analysis is only performed on the central core of the tract, i.e. the skeleton. This is because thickness and mis-registration errors increase with radial distance from the central core.

With larger, thicker fiber tracts, such as the corpus callosum, this method misses axonal injuries that do not include the central core of the fiber tract.

Voxel-based analysis (VBA) is somewhat less reliable, even with weighting, at the periphery of the brain, where fiber tracts are small distal branches of larger tracts. On the other hand, VBA includes the full thickness of a fiber tract, relying on previously described steps 1, 2, 4 and 5 to minimize mis-registration errors.

Thus, both TBSS and VBA have strengths and weaknesses. The combined use of VBA and TBSS statistical maps (e.g., by averaging together) will reinforce voxels that meet statistical significance on both maps while suppressing voxels which are significant on only one map. The net effect will likely be to underestimate the number of voxels with truly reduced FA values (false negatives). But more important is the reduction in the number of voxels incorrectly identified as having reduced FA values (false positives). The present embodiment of the disclosure preferably combines TBSS and VBA to create a single statistical probability map.

5. Co-Registration and Fusion of Multiple MR Scan Types (e.g., SWI. DTI. FLAIR-T2) into the Same Three Dimensional Space As exemplified in FIG. 6, these three MR sequences reveal a number of pathological consequences of head trauma. SWI reveals markers of hemorrhage, including contusion, subarachnoid, subdural, parenchymal and venous microhemorrhage and areas of increased deoxyhemoglobin. FLAIR/T2 will reveal on visual inspection a subset of axonal injuries which result in edema or glial scarring. DTI will reveal white matter axonal injury at many stages and is more sensitive than FLAIR/T2 but requires post-processing to identify.

Having these multiple image types with their respective lesions in the same spatial reference frame is useful and allows the clinician or researcher to infer the biomechanical events on the head and brain as well as to better survey the extent and type of pathology by region.

One aspect of the disclosure uses registration programs from SPM8 or FSL to put the different image types into the same spatial reference frame, using lab-made templates for each image type. The optional final step uses for example the program MRIcro (www.mccauslandcenter.sc.edu/mricro) to produce 3-D renderings of pairs of image types. Typically, for instance, a thresholded DTI FA statistical map will be overlaid or fused with a FLAIR or SWI image to show the spatial relationship between different lesion types.

A second aspect of the disclosure is illustrated schematically in FIGS. 7-15. It relates to a semi-automated method of detection and quantification of small hemorrhages using susceptibility-weighted images (SWI). As previously described, various embodiments according to the present disclosure process the SWI images for combination or fusion with corresponding DTI images.

SWI has been shown to be the MRI sequence that is most sensitive to iron due to iron's high paramagnetic susceptibility. This property means that SWI is also the most sensitive sequence for detecting blood products, including hemosiderin which is a permanent marker of prior hemorrhage. Further, it has been shown that the number of bleeds and the total volume of bleeding is predictive of a clinical outcome from TBI. Automated and semi-automated methods of identification (segmentation) and quantification are in general more efficient, objective and sensitive than manual methods of lesional analysis in medical imaging.

Another aspect of this disclosure gives an optional yet reliable method of detection and quantification of small venous and subarachnoid hemorrhages in the white matter, which can be detected at all severity levels of TBI. One strength of this portion of the disclosure is the ability to exploit multichannel image differential sensitivities to iteratively remove artifacts and isolate the hemorrhages. A description of one exemplary but non-limiting procedure now follows.

Figure 8:
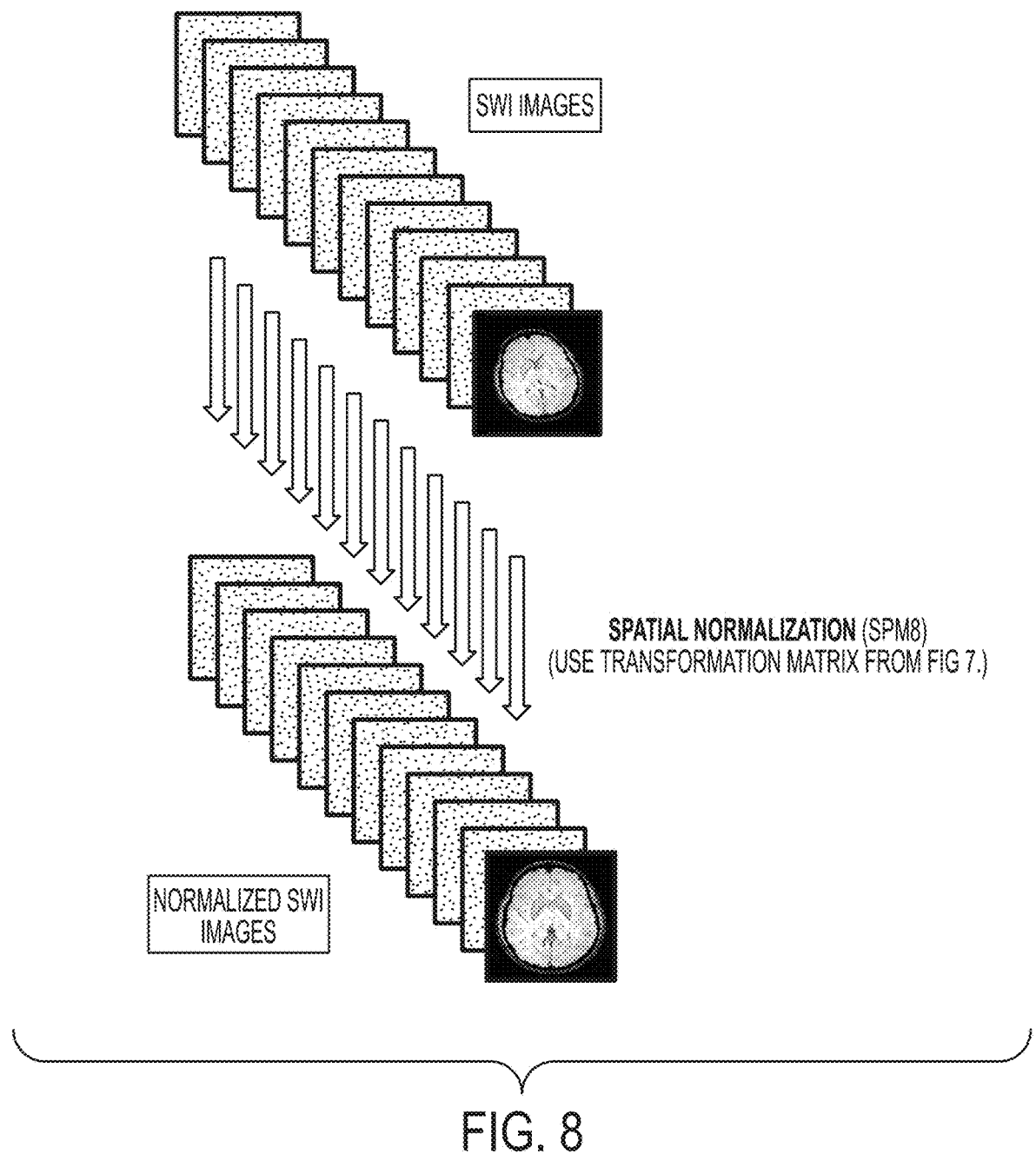
FIG. 8 illustrates spatial normalization of SWI images using the transformation matrix as illustrated in FIG. 7 according to embodiments of the disclosure.
Figure 9:
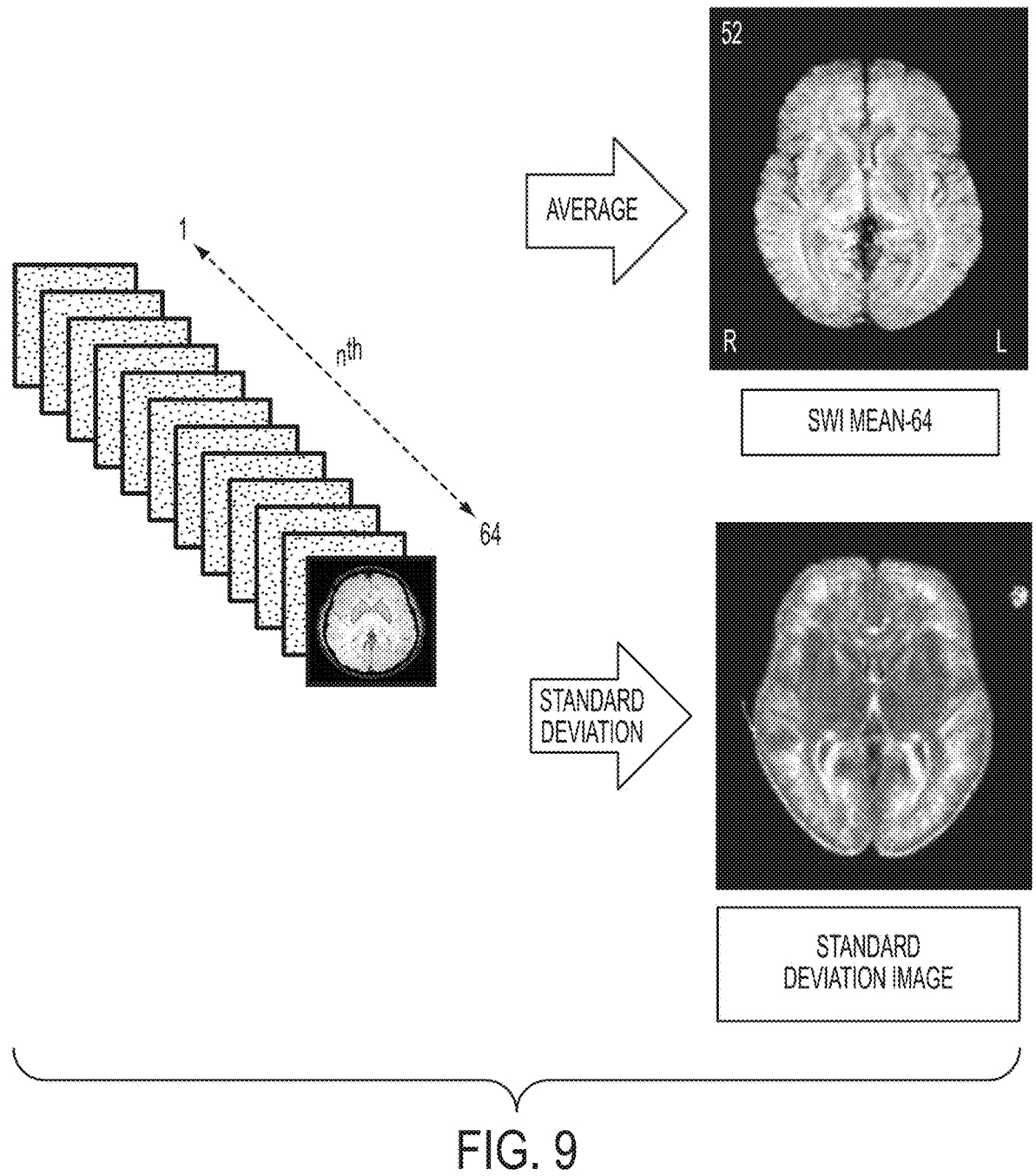
FIG. 9 illustrates creation of an SWI template using the normalized SWI images and calculation of statistical mean and standard deviation images according to embodiments of the disclosure.
Figure 10:
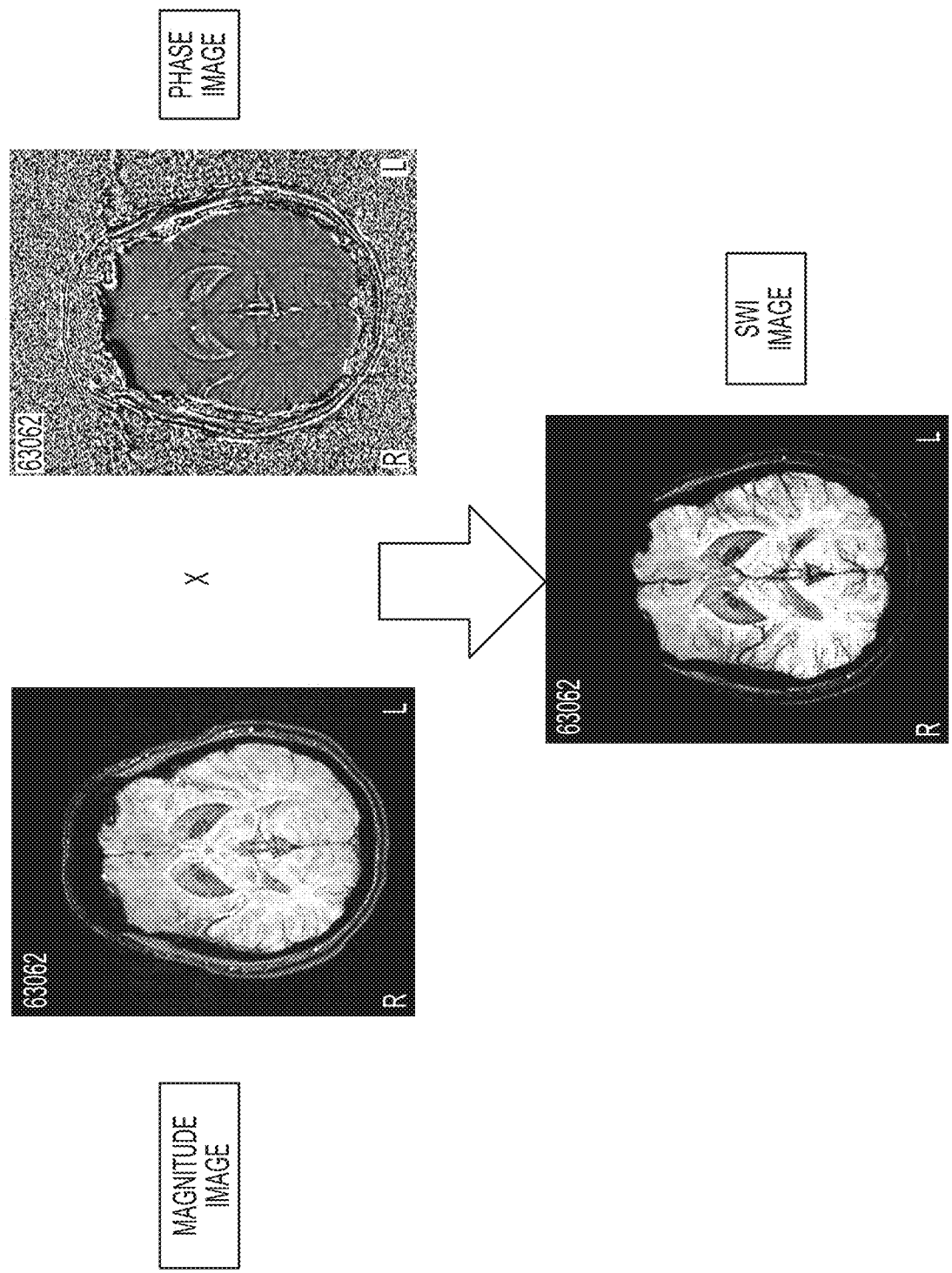
FIG. 10 illustrates creation of a combined SWI image based on corresponding magnitude and phase images according to embodiments of the disclosure.

1. Each of 64 healthy controls' T2 images (see FIG. 7) were nonlinearly normalized (using for example SPM8) to the T2 template in SPM8's template options in the spatial normalization function. The resulting transformation matrix was applied to each subject's SWI image (shadow transformation) (FIG. 8).

2. A new template (FIG. 9) was created by averaging the 64 normalized images together (e.g., by the imcalc image calculator in SPM8).

3. A standard deviation map (FIG. 9) was calculated from the 64 spatially normalized images (imcalc/SPM8)

Figure 11:
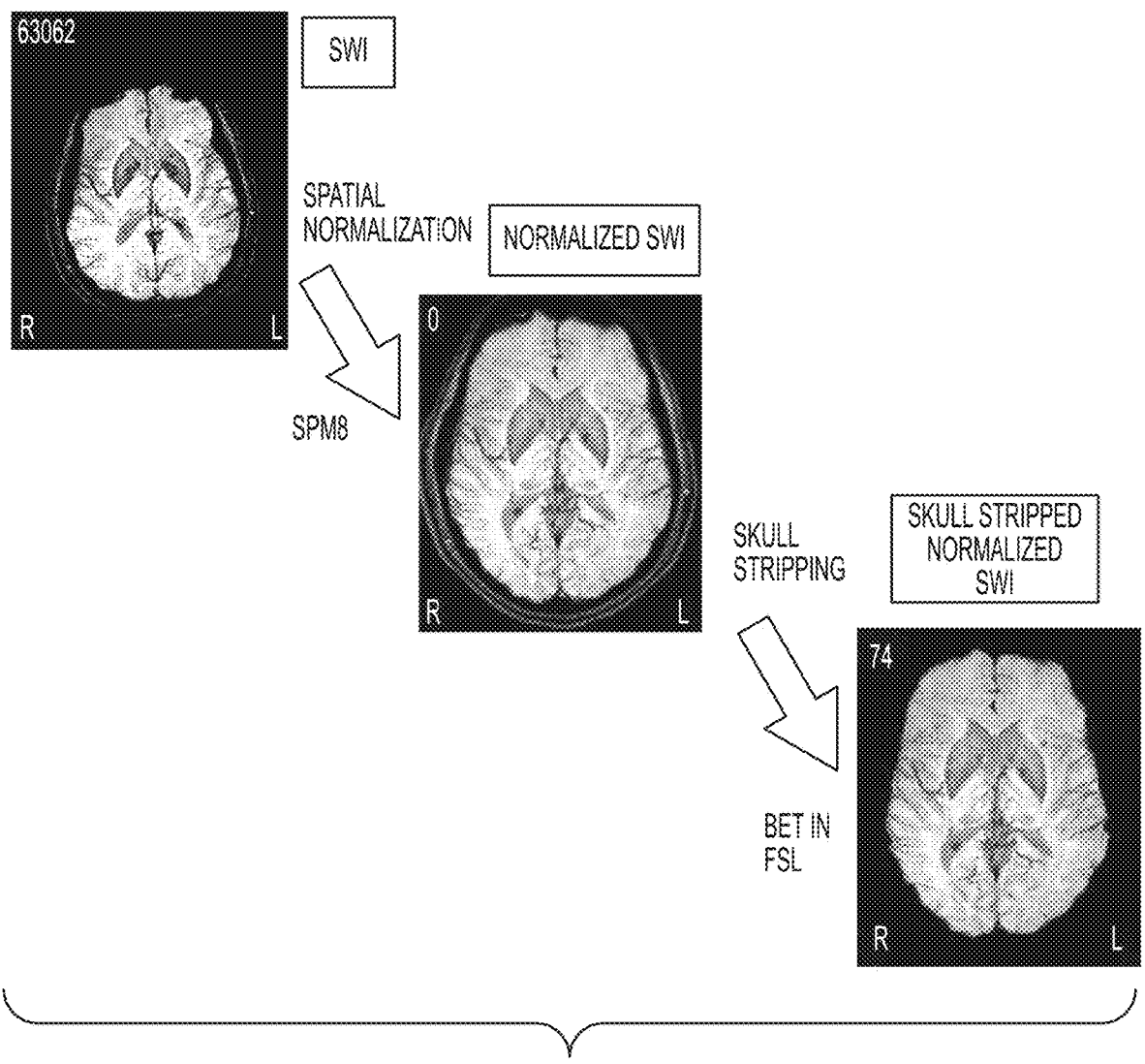
FIG. 11 illustrates a representative embodiment of spatial normalization and skull stripping of an SWI image using an SWI template generated as illustrated in FIG. 9.
Figure 12:
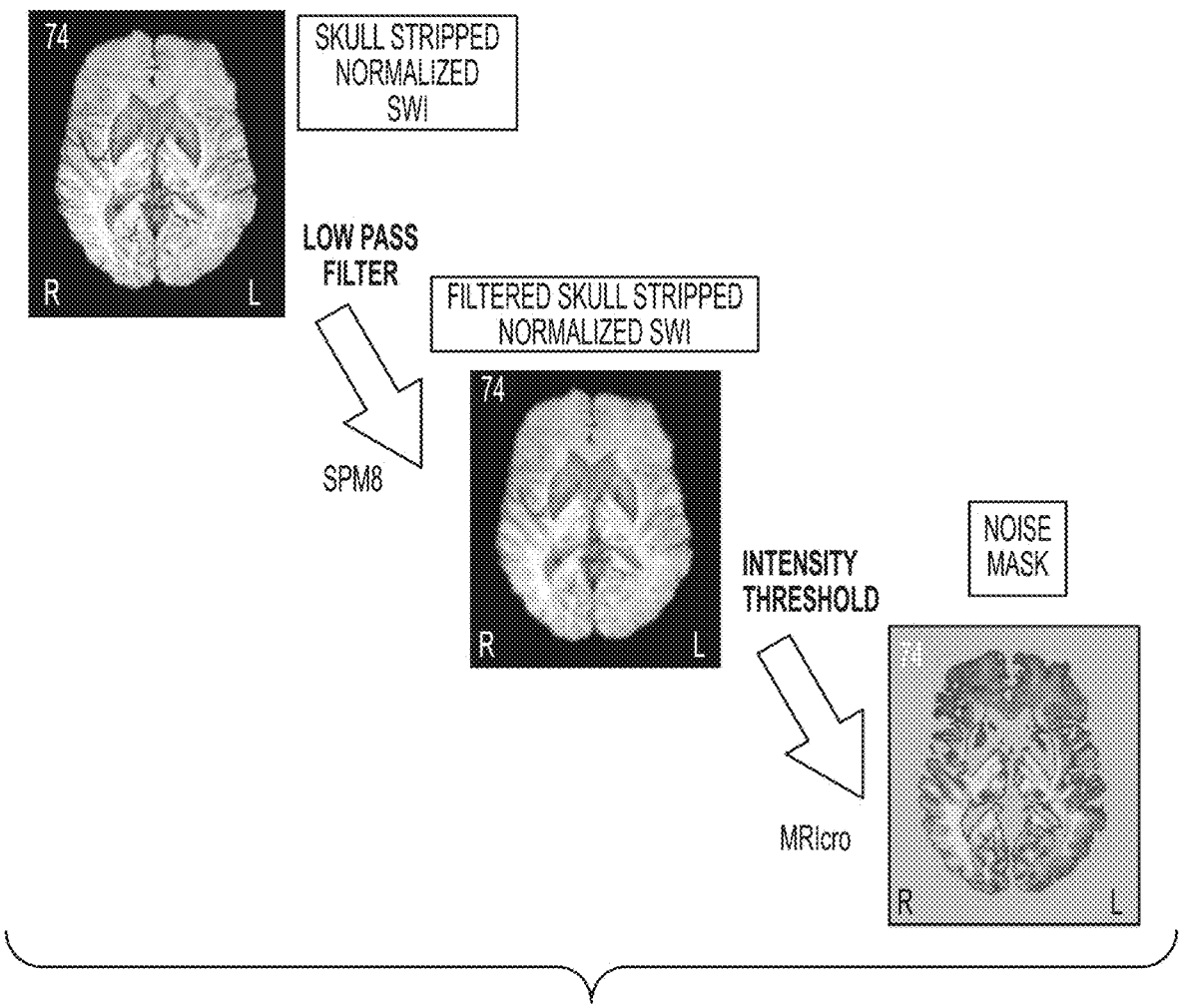
FIG. 12 illustrates creation of a noise mask based on a normalized and skull stripped SWI image according to embodiments of the disclosure.
Figure 13:
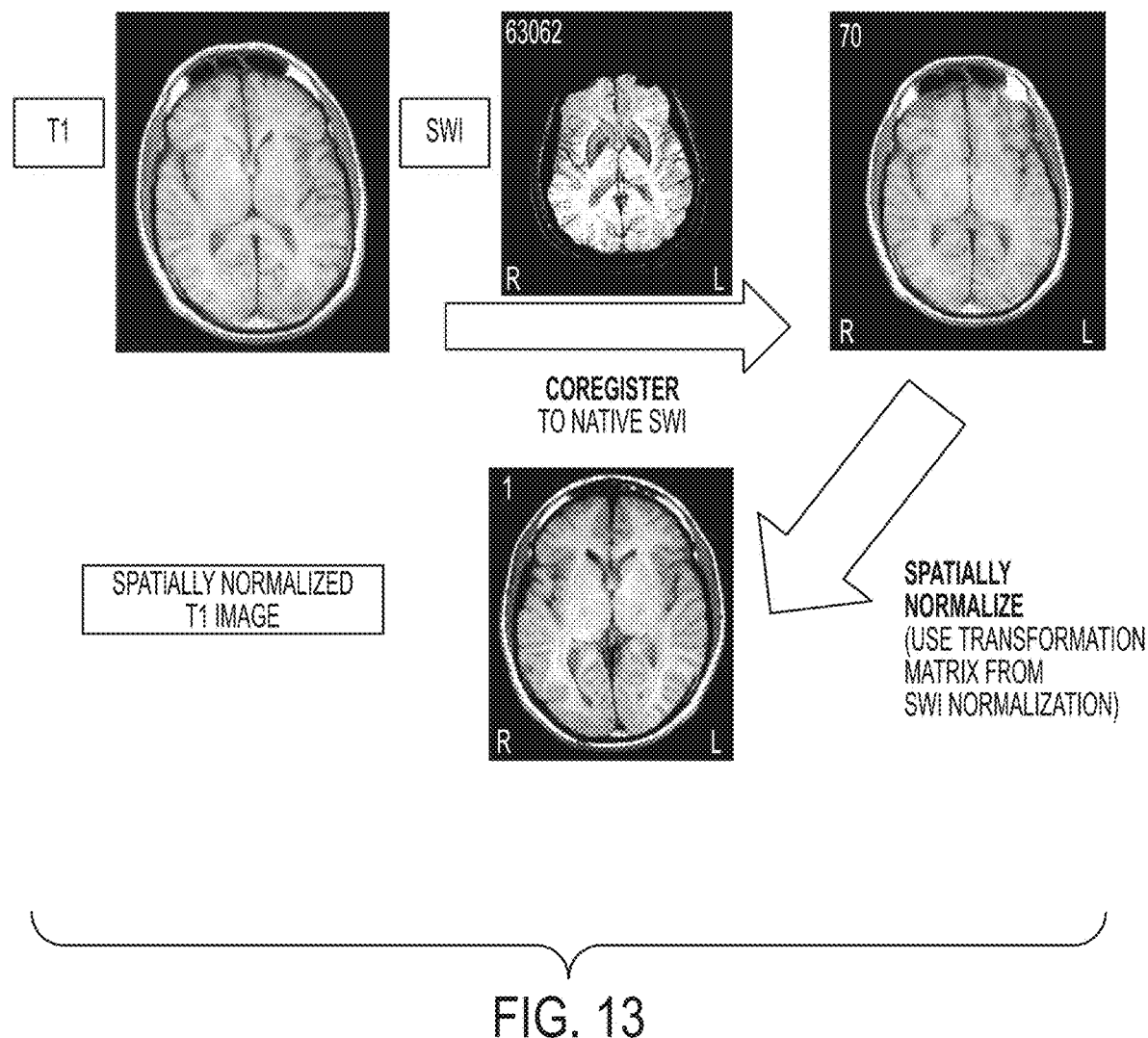
FIG. 13 illustrates co-registration of a single subject T1 image and SWI image followed by shadow transformation using a transformation matrix as illustrated in FIG. 7.

4. Creation of normalized SWI image: SWI data is processed (phase×magnitude image) (FIG. 10) and resultant image is normalized using the SW7-64 template (FIG. 11).

5. Skull strip normalized SWI image (FIG. 11): The resulting normalized SWI image is skull stripped using the BET function in FSL (see e.g., http://fsl.fmrib.ox.ac.uk/fsl/fsl-4.1.9/bet2).

6. Creation of a noise mask (FIG. 12): A low pass filter is applied to the native SWI image and then a lower signal threshold (e.g., using MRIcro: "ROI options") is applied to remove sulci, some vessels, external brain contour differences between patient and template, and low signal artifacts in the upper and lower slices.

7. Co-register ("coregistration" function in SPM8) the patient's T1 image with the native SWI image (FIG. 13): The co-registered T1 image is then "shadow transformed" by using the transformation matrix created during the prior SWI normalization to create a normalized T1 image.

8. Co-register the patient's FLAIR image with the native SWI image: The co-registered FLAIR image is then "shadow transformed" by using the transformation matrix rile created during the prior SWI normalization to create a normalized FLAIR image.

Figure 14:
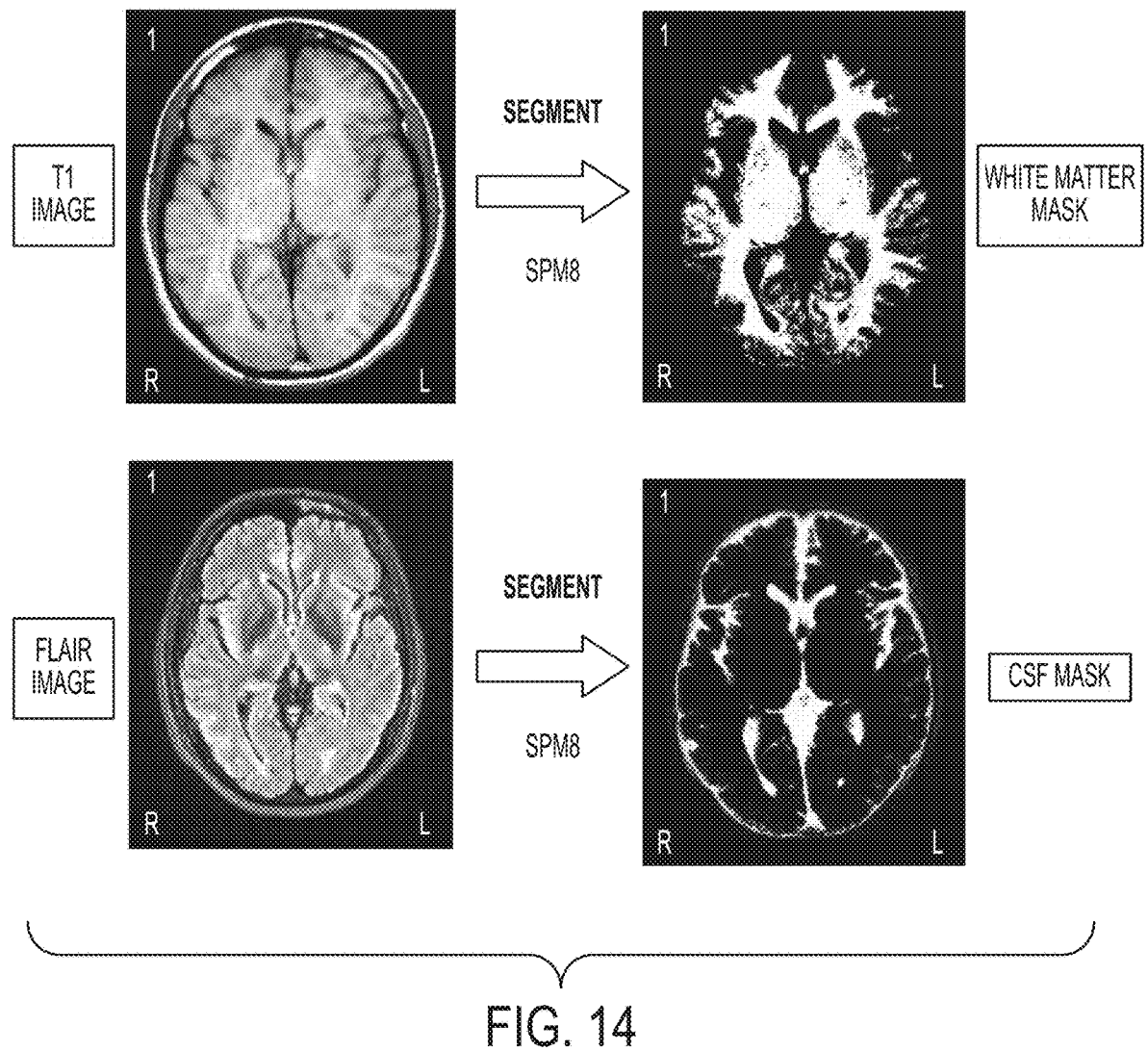
FIG. 14 illustrates segmentation of FLAIR and T1 images to create a cerebrospinal fluid (CSF) mask and white matter mask, respectively, according to embodiments of the disclosure.
Figure 15:
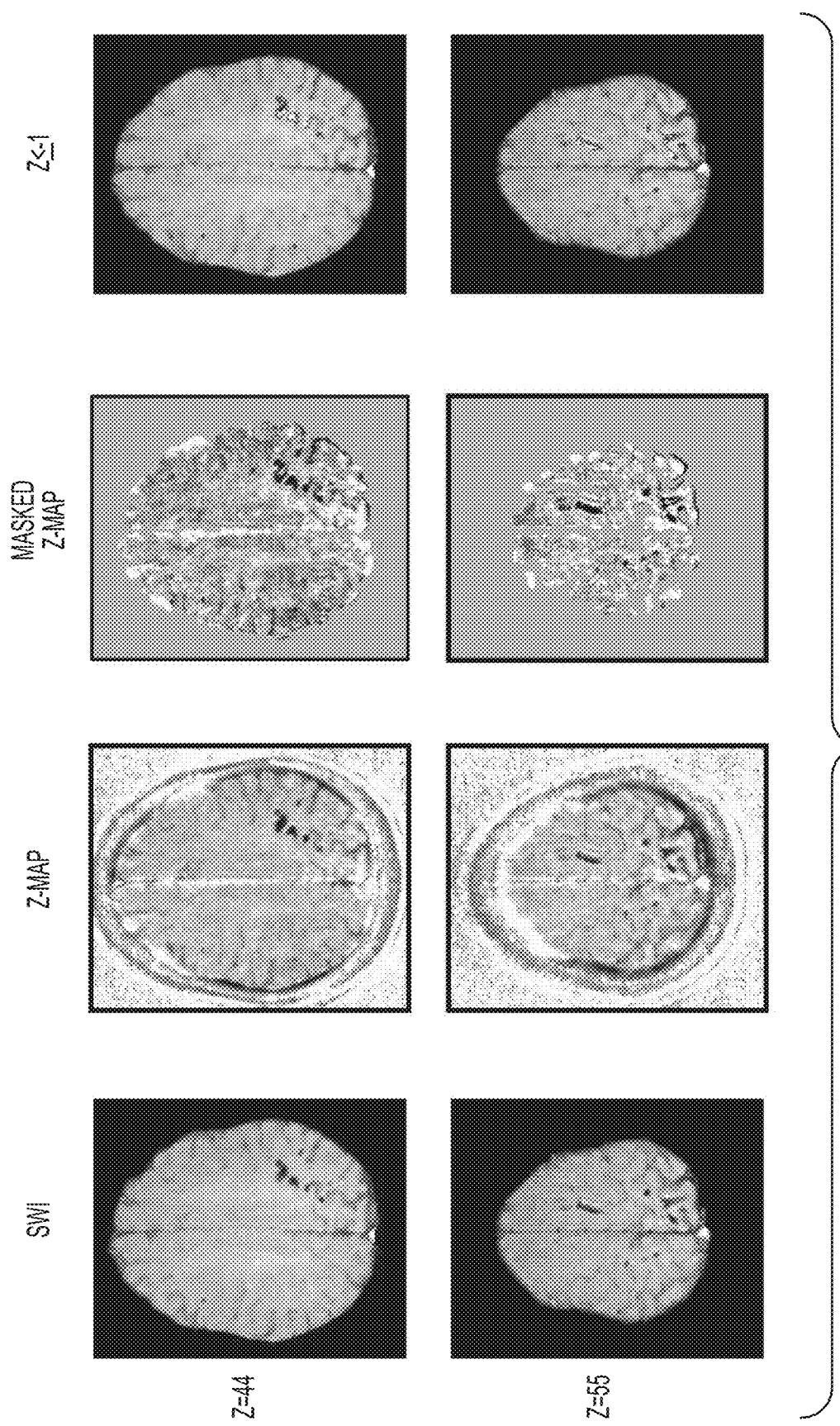
FIG. 15 illustrates additional processing of the SWI image to generate a volume measurement of total hemorrhagic lesion volume according to embodiments of the present disclosure.

9. Segment both the T1 and FLAIR images separately, using the segmentation function in SPM8 (FIG. 14).

10. Creation of white matter mask and CSF mask (FIG. 14): A white matter probability image obtained in Step 7 is intensity thresholded to form a white matter mask and a CSF mask is created analogously using the CSF probability image obtained in Step 8.

11. Creation of z-map (FIG. 15): A voxel-wise z-map is calculated for the patient's normalized SWI image (from Step 5), the SWI-64 template (Step 2) and its standard deviation image (Step 3) according to the formula for the z-statistic:

$z_i = (X_i - \mu_i)/\sigma_i$, where $X_i$ is the ith voxel FA value,
$\mu_i$ is the mean FA for the 64 controls at the ith voxel, and
$\sigma_i$ is the standard deviation of the 64 voxel FA values at the ith voxel.

12. Apply masks to z-map—multiply noise, CSF, white matter, blood vessel binary masks to z-map to remove all but white matter.

13. Threshold z-map: Use an empirically determined threshold, e.g., at z<−1, to identify micro-hemorrhages in z-map.

14. Volume measurement-Create a binary mask of total hemorrhagic lesion volume using "ROI options" in MRIcro using "apply intensity filter to volume" option with z<−1 and then saving the ROI. Read out volume by multiplying number of voxels obtained from "histogram" tool in MRIcro by the volume of a single voxel.

As those of ordinary skill in the art will recognize from the above representative embodiments, computer implemented processing of MR images according to the present disclosure provides various advantages. For example, combination of three MR sequences may be used to reveal a number of pathological consequences of head trauma. SWI reveals markers of hemorrhage, including contusion, subarachnoid, subdural, parenchymal and venous microhemorrhage and areas of increased deoxyhemoglobin. FLAIR/T2 will reveal on visual inspection a subset of axonal injuries which result in edema or glial scarring. DTI will reveal white matter axonal injury at many stages and is more sensitive than FLAIR/T2 but requires post-processing to identify.

Spatial normalization and correction for age according to the present disclosure facilitates statistical combination of MR data acquired using different scanning devices and/or protocols to generate control subject templates that can be more accurately compared to images from a single subject for use in clinical diagnosis of TBI. Having these multiple image types with their respective lesions in the same spatial reference frame is useful and allows the clinician or researcher to infer the biomechanical events on the head and brain as well as to better survey the extent and type of pathology by region.

The processes, methods, or algorithms disclosed herein can be deliverable to/implemented by a processing device, controller, or computer, which can include any existing programmable electronic control unit or dedicated electronic control unit. Similarly, the processes, methods, or algorithms can be stored as data and instructions executable by a controller or computer in many forms including, but not limited to, information permanently stored on non-writable storage media such as ROM devices and information alterably stored on writeable storage media such as floppy disks, magnetic tapes, CDs, RAM devices, and other magnetic and optical media. The processes, methods, or algorithms can also be implemented in a software executable object. Alternatively, the processes, methods, or algorithms can be embodied in whole or in part using suitable hardware components, such as Application Specific Integrated Circuits (ASICs), Field-Programmable Gate Arrays (FPGAs), state machines, controllers or other hardware components or devices, or a combination of hardware, software and firmware components.

While exemplary embodiments are described above, it is not intended that these embodiments describe all possible forms encompassed by the claims. The words used in the specification are words of description rather than limitation, and it is understood that various changes can be made without departing from the spirit and scope of the disclosure. As previously described, the features of various embodiments can be combined to form further embodiments of the invention that may not be explicitly described or illustrated.

While various embodiments may have been described as providing advantages or being preferred over other embodiments or prior art implementations with respect to one or more desired characteristics, those of ordinary skill in the art recognize that one or more features or characteristics can be compromised to achieve desired overall system attributes, which depend on the specific application and implementation. As such, embodiments described as less desirable than other embodiments or prior art implementations with respect to one or more characteristics are not outside the scope of the disclosure and can be desirable for particular applications.

The invention claimed is:

1. A method for processing brain images, comprising:
storing an image template formed from combining a plurality of spatially normalized source brain images of a plurality of control subjects;
storing a brain image of a single subject;
normalizing the brain image of the single subject using the image template formed from the plurality of control subjects;
calculating a statistical parameter that compares the brain image of the single subject to the image template for each voxel in each image to generate a statistical map of the single subject;
applying a mask to the statistical map of the single subject to remove non-white matter and generate a white matter statistical map of the single subject; and
calculating a volume of hemorrhagic lesions based on a number of voxels in the white matter statistical map where the statistical parameter exceeds a corresponding threshold, wherein storing an image template comprises:
storing a plurality of T2 source brain images of the plurality of control subjects;
storing a plurality of susceptibility-weighted (SWI) images of the plurality of control subjects;
generating a plurality of normalized T2 images based on the plurality of T2 source brain images and a T2 image template;
combining the plurality of normalized T2 images to generate a transformation matrix;
applying the transformation matrix to each of the SWI images of the plurality of control subjects to generate a plurality of normalized SWI images; and
combining the normalized SWI images to generate the image template.

2. The method of claim 1 wherein combining the normalized SWI images comprises:
calculating a mean value of corresponding voxels of the normalized SWI images; and
calculating a standard deviation of corresponding voxels of the normalized SWI images.

3. The method of claim 1 further comprising skull stripping the normalized brain image of the single subject prior to applying the mask.

4. The method of claim 1 wherein applying the mask comprises:
applying a low pass filter to the brain image of the single subject;
applying a cerebrospinal fluid (CSF) mask; and
applying a white matter mask.

5. The method of claim 4 wherein applying a CSF mask comprises:
co-registering the brain image of the single subject with a fluid attenuated inversion recovery (FLAIR) image of the single subject;
generating a normalized FLAIR image based on the FLAIR image and the image template;
segmenting the normalized FLAIR image to isolate white matter and generate a segmented normalized FLAIR image; and
thresholding the segmented normalized FLAIR image.

6. The method of claim 4 wherein applying a white matter mask comprises:
co-registering the brain image of the single subject with a T1 image of the single subject;
generating a normalized T1 image based on the T1 image and the image template;
segmenting the normalized T1 image to isolate white matter and generate a segmented normalized T1 image; and
thresholding the segmented normalized T1 image.

7. The method of claim 1 wherein combining the normalized SWI images comprises:
calculating a mean value of corresponding voxels of the normalized SWI images; and
calculating a standard deviation of corresponding voxels of the normalized SWI images.

8. The method of claim 1 wherein calculating a statistical parameter comprises calculating a z-score for each voxel of a white matter brain image of the single subject relative to a corresponding voxel of the template.

9. The method of claim 8 wherein the z-score is based on a mean value and standard deviation of a fractional anisotropy (FA) value for each voxel.

10. A computer-implemented method for processing brain images for diagnosis of traumatic brain injury of a single subject in a clinical setting, comprising:
storing an image template formed from combining a plurality of spatially normalized source brain images of a plurality of control subjects;
storing a brain image of the single subject;
normalizing the brain image of the single subject using the image template formed from the plurality of control subjects;
calculating a statistical parameter that compares the brain image of the single subject to the image template for each voxel in each image to generate a statistical map of the single subject;
applying a mask to the statistical map of the single subject to remove non-white matter and generate a white matter statistical map of the single subject; and
calculating a volume of hemorrhagic lesions based on a number of voxels in the white matter statistical map where the statistical parameter exceeds a corresponding threshold;

wherein storing an image template comprises:
storing a plurality of T2 source brain images of the plurality of control subjects:
storing a plurality of susceptibility-weighted (SWI) images of the plurality of control subjects;
generating a plurality of normalized T2 images based on the plurality of T2 source brain images and a T2 image template;
combining the plurality of normalized T2 images to generate a transformation matrix;
applying the transformation matrix to each of the SWI images of the plurality of control subjects to generate a plurality of normalized SWI images; and
combining the normalized SWI images to generate the image template.

11. The method of claim 10 wherein combining the normalized SWI images comprises:
calculating a mean value of corresponding voxels of the normalized SWI images; and
calculating a standard deviation of corresponding voxels of the normalized SWI images.

12. The method of claim 10 wherein calculating a statistical parameter comprises calculating a z-score for each voxel of the white matter brain image of the single subject relative to a corresponding voxel of the template.

13. The method of claim 12 wherein the z-score is based on a mean value and standard deviation of a fractional anisotropy (FA) value for each voxel.

14. The method of claim 10 further comprising skull stripping the normalized brain image of the single subject prior to applying the mask.

15. The method of claim 10 wherein applying a mask comprises:
applying a low pass filter to the brain image of the single subject;
applying a cerebrospinal fluid (CSF) mask; and
applying a white matter mask.

16. The method of claim 15 wherein applying a CSF mask comprises:
co-registering the brain image of the single subject with a fluid attenuated inversion recovery (FLAIR) image of the single subject;
generating a normalized FLAIR image based on the FLAIR image and the image template;
segmenting the normalized FLAIR image to isolate white matter and generate a segmented normalized FLAIR image; and
thresholding the segmented normalized FLAIR image.

17. The method of claim 15 wherein applying a white matter mask comprises:
co-registering the brain image of the single subject with a T1 image of the single subject;
generating a normalized T1 image based on the T1 image and the image template;
segmenting the normalized T1 image to isolate white matter and generate a segmented normalized T1 image; and
thresholding the segmented normalized T1 image.

18. The method of claim 10 wherein the brain image of the single subject is a susceptibility weighted (SWI) image.

* * * * *